(12) United States Patent
Chen et al.

(10) Patent No.: US 8,304,716 B2
(45) Date of Patent: Nov. 6, 2012

(54) SAMPLING DEVICE FOR ION MIGRATION SPECTROMETER AND METHOD FOR USING THE SAME, AND ION MIGRATION SPECTROMETER

(75) Inventors: Zhiqiang Chen, Beijing (CN); Yuanjing Li, Beijing (CN); Hua Peng, Beijing (CN); Zhongxia Zhang, Beijing (CN); Xin Xue, Beijing (CN); Yaoxin Wang, Beijing (CN); Jin Lin, Beijing (CN); Xiaohui Yang, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 13/170,763

(22) Filed: Jun. 28, 2011

(65) Prior Publication Data
US 2012/0168617 A1    Jul. 5, 2012

Related U.S. Application Data

(63) Continuation of application No. PCT/CN2011/073629, filed on May 4, 2011.

(51) Int. Cl.
*B01D 59/44* (2006.01)
*H01J 49/00* (2006.01)

(52) U.S. Cl. ........ 250/282; 250/281; 250/287; 250/288; 250/290; 250/291; 250/292

(58) Field of Classification Search .......... 250/281–283, 250/287–292
See application file for complete search history.

(56) References Cited

U.S. PATENT DOCUMENTS
5,083,019 A * 1/1992 Spangler ........................ 250/286
(Continued)

FOREIGN PATENT DOCUMENTS
| CN | 2927049 Y | 7/2007 |
|---|---|---|
| CN | 101819179 A | 9/2010 |
| JP | 2005207884 A | 8/2005 |

OTHER PUBLICATIONS

PCT/ISA/220 International Search Report for corresponding PCT/CN2011/073629 (mailed Oct. 13, 2011) (in Chinese).

*Primary Examiner* — Jack Berman
*Assistant Examiner* — Meenakshi Sahu
(74) *Attorney, Agent, or Firm* — Elizabeth N. Spar; Kathleen M. Williams; Edwards Wildman Palmer LLP

(57) ABSTRACT

The present invention discloses a sampling device for an ion migration spectrometer (IMS), comprising: an inner sleeve part, inside of which an inner cavity is defined, one end of the inner sleeve part is connected with an inlet of an migration pipe via an inner-layer channel, and the other end of the inner sleeve part is configured with an inner end cap having an inner opening; and an outer sleeve part, which is configured as an eccentric sleeve that is coaxial with the inner sleeve part and able to rotate with respect to the inner sleeve part, so as to form a sleeve cavity between the inner sleeve part and the outer sleeve part, wherein one end of the outer sleeve part is configured with at least one connecting opening that is selectively connected with the inner-layer channel, and the other end of the outer sleeve part is configured with an outer end cap, on which a first outer opening selectively connected with the inner opening and a second outer opening selectively connected with the sleeve cavity are configured, wherein the outer end cap is configured to be able to rotate between a first location and a second location with respect to the inner end cap, so as to selectively introduce a sample to be detected into the inner-layer channel via one of the inner cavity and the sleeve cavity. Moreover, the present invention further relates to a method for solid and gas sampling by using the above sampling device.

17 Claims, 3 Drawing Sheets

U.S. PATENT DOCUMENTS

| | | | |
|---|---|---|---|
| 5,162,652 A * | 11/1992 | Cohen et al. | 250/288 |
| 5,691,206 A * | 11/1997 | Pawliszyn | 436/178 |
| 6,042,787 A * | 3/2000 | Pawliszyn | 422/69 |
| 6,604,406 B1 * | 8/2003 | Linker et al. | 73/28.02 |
| 6,884,997 B2 | 4/2005 | Kashima et al. | |
| 7,131,341 B2 * | 11/2006 | Wareham et al. | 73/864.71 |
| 7,404,932 B2 * | 7/2008 | Chen et al. | 422/535 |
| 7,674,631 B2 * | 3/2010 | Pawliszyn | 436/178 |
| 8,178,045 B2 * | 5/2012 | Cambron et al. | 422/69 |

\* cited by examiner

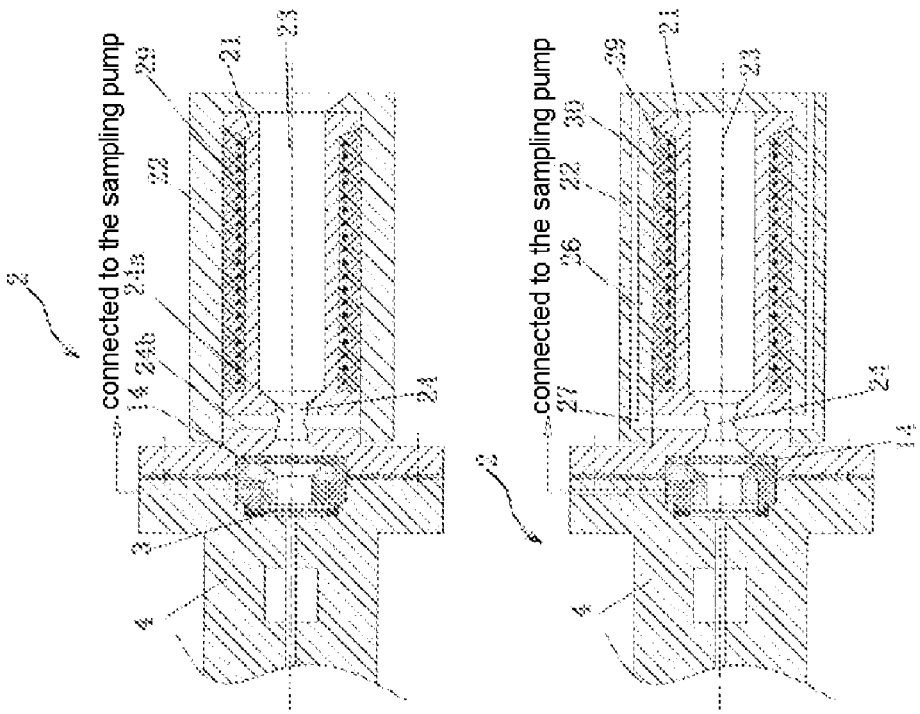
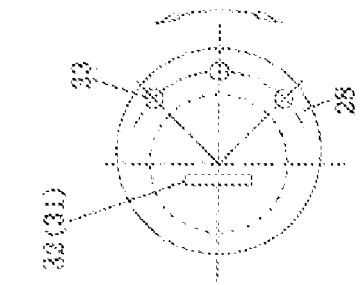 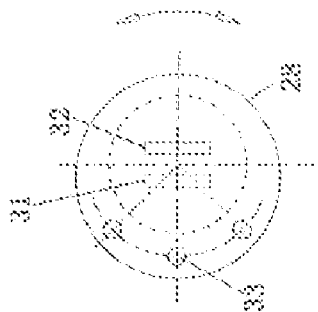
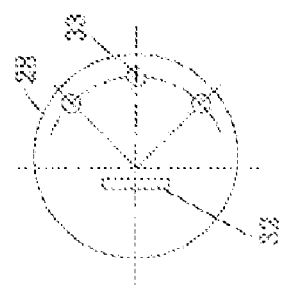 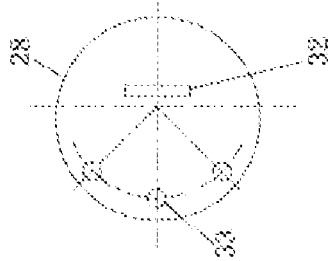
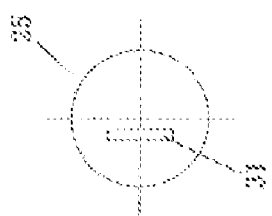 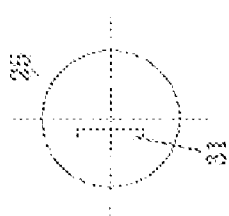
Fig.2A　　　　　　　　Fig.2B
Fig.2

SAMPLING DEVICE FOR ION MIGRATION SPECTROMETER AND METHOD FOR USING THE SAME, AND ION MIGRATION SPECTROMETER

CROSS-REFERENCE TO RELATED APPLICATIONS

This application is a continuation of PCT International Application No. PCT/CN2011/073629, which was filed May 4, 2011, which claimed the priority of Chinese Patent Application 201010624253.8, filed Dec. 31, 2010, the entireties of each of which are hereby incorporated by reference.

FIELD OF THE INVENTION

The present invention relates to the field of ion migration detection technologies, and in particular, to a sampling device for an ion migration spectrometer and a method for detecting samples to be detected of solid particles and gas by using said sampling device. Moreover, the invention further relates to an ion migration spectrometer provided with the above sampling device.

BACKGROUND OF THE INVENTION

A detecting instrument based on ion migration spectrum (IMS) technologies may be used for detecting trace-level prohibited articles such as explosives, drugs and toxic chemicals, etc. Due to the characteristics of quick speed, sensitiveness and portability, etc., such detecting instrument has now been widely used in military and safety inspection fields. Most of the commercialized portable IMS instruments adopt two sampling methods, that is, solid sampling or wiping sampling, and gas sampling. The former collects particles to be detected by wiping the surface of a suspicious object with a clean sampling carrier, for example, wipe paper, then puts the wipe paper or the sampling carrier adhering with the sample particles to the instrument inlet, and gasifies the solid explosives for analyzing through the method of thermal desorption. During the sampling and testing processes, the operator needs to wear gloves or to use a customized wiping sampler furnished with a sampling carrier in order to avoid polluting the sampling carrier and the detecting instrument. The latter sucks the gas atmosphere or the vaporous sample on the solid surface, which is to be detected, into the sampling device of the instrument for analyzing, via a suction pump directly.

The gas sampling method is easy to operate, no consumable is needed, and it may avoid to directly contacting the object to be detected. However, because the vapor pressure of most objects to be detected, for example, explosives and drugs, is very low (below ppb), it is difficult to reach the lower limit of detection of an instrument simply by the collecting mode of sucking a sample directly. If a preconcentration or preenrichment device is configured on the front end of an analyzing system, the detection capability of the instrument may be improved greatly. A preconcentrator mainly comprises an adsorbing material and a heater, and its operational principle lies in that the gas to be detected is first passed through the adsorbing material for enrichment, and after a certain period of time, the gas absorbed is resolved in a short time by heating the adsorbing material, so that a higher gas concentration may be obtained. Some commercialized instruments, for example, VaporTracer from GE, employ an external portable vacuum suction device for collecting gas samples, wherein a sampling carrier is first placed in the suction port of the vacuum device, and molecules of an object to be detected are captured thereon after an air containing the vapor of the object to be detected is passed through the sampling carrier for a certain period of time, then the sampling medium is placed into the detector and the molecules of the object to be detected are released for analyzing via the method of thermal desorption; therefore, the device actually plays a role of sample enrichment.

At present, there are a plurality of related patents that respectively describe a preconcentration device for an ion migration spectrometer or other analyzing instrument of the same type. U.S. Pat. No. 5,162,652 describes a technology of sample mixing, concentrating and introducing, in which a part of the gas in a sealed luggage is extracted and combined with the ambient atmosphere in a closed cavity, the mixed sample is passed through a collector, and certain molecules to be detected are aggregated onto a collecting surface for concentration, then the molecules absorbed are released from the surface and sent to an ion migration spectrometer for analyzing. U.S. Pat. No. 6,604,406 describes a preconcentration device that can be manually carried, in which an object is captured via a permeable mesh screen, and then the materials of the object are released into a cavity by heating. U.S. Pat. No. 5,083,019 describes an absorbing probe concentration device, in which an absorbing probe made of a metallic filament coil having an absorbing coating is placed in a sampling gas flow at a low temperature, the gas sample is collected via its surface, and during the testing process, the probe is manually fed into a ionization reaction zone of the ion migration device via a slide shaft and then heated rapidly, so that the material to be detected is resolved and ionized. Patent application WO2007091998 describes a concentration technology of solid phase micro-extracting optical fiber collection, in which a solid phase micro-extracting optical fiber exposed in air is employed to collect a sample of explosives, taggants or a mixture thereof, and after thermal desorption, the optical fiber is put into a preconcentration device for concentrating the sample, and then the sample is fed into an ion migration spectrometer for detecting. Patent US20090249958 describes a device component that may replace the concentration carrier, wherein the device component is consisted of a housing and an inner rack, and a cavity that may accommodate several concentration carriers and a channel that accesses to a sampling device of a detecting instrument are formed via a retractable spring compressing device, thus the material collected by the concentration carrier may be brought into the instrument for analyzing via a consecutive gas flow. The concentration device disclosed in patent application WO2008074981 is located inside the ion migration sampling device, a small negative pressure and a small positive pressure are alternately applied to the pipe cavity via a pulse pressure generator connected with the migration pipe cavity, so that an air is sucked into or evacuated from the sampling device in a mode that emulates gasping, thus the component to be detected is effectively absorbed by the preconcentration device, instead of entering the ionization zone, and after the component to be detected is accumulated for a certain period of time, the pressure generator generates a larger negative pressure, so that the object to be detected that is released by the preconcentration device is sucked into the ionization zone inside the instrument for analyzing. The preconcentration device described in patent application WO2007113486 is connected with the inlet of an ion migration spectrometer, wherein the preconcentration device is formed by a metal pipe of which the inner surface has a layer of silastic adsorbing material, and a resistance heating element connected with a power is configured under the absorbing layer for periodically heating the silastic absorbing layer, so that the material absorbed is desorbed and released to an ion migration spectrometer at a higher concentration.

In practical application, because at present, solid wiping sampling is still the sample collecting mode commonly used by the ion migration instrument, a sampling carrier sampling device and a thermal resolver for heating the carrier are often configured on the front end of the instrument. In order not to influence the solid sampling device and the function of the instrument, the concentrator described in the above patents/patent applications (for example, U.S. Pat. Nos. 5,162,652, 6,604,406, WO2007091998 and US20090249958, etc.) generally employs an external design and needs a separate device that is independent of the instrument, and after sample collection is accomplished, sampling is performed in the same mode as solid sampling, thereby the process of the whole detecting operation is made boresome and complex; on the other hand, in an IMS instrument with a built-in concentrator (for example, WO2008074981 and WO2007113486, etc.), because the absorbing element in the concentrator needs to work at a low temperature, no thermal resolver is configured on the front end of the instrument, thus the instrument can only be used for analyzing a gas sample.

Therefore, a more practical IMS instrument that has the functions of solid sampling and gas sampling simultaneously needs to be developed in the prior art. On one hand, it has a built-in concentration device, for simplifying instrument configuration and operation procedure; on the other hand, it may perform a sensitive and facile detection on a trace-amount solid residual and an extremely low concentration gas atmosphere of an object to be detected.

SUMMARY OF THE INVENTION

Therefore, it is an object of the present invention to solve at least one aspect of the above problems and defects in the prior art.

Accordingly, directed to the shortages in the design of the above existing ion migration spectrum trace-amount analyzing instrument that may detect a gas sample, it is one of the objects of the invention to put forward a design of a novel sampling device for an ion migration spectrometer, and a method for using the same, wherein a solid particle sample analyzing function and a low-concentration gas analyzing function are integrated in a single instrument, so that the functions of solid sampling and gas sampling can be achieved simultaneously by the same sampling device.

A further object of the invention is to provide a design of a novel sampling device for an ion migration spectrometer and a method for using the same, wherein no additional gas sample collection and concentration device is needed, moreover, not only the operation procedure can be simplified and the sensitivity and analyzing efficiency on the gas sample can be improved, but also an effective detection on a trace-amount of a solid sample may be realized at the same time.

According to one aspect of the present invention, it provides a sampling device for an ion migration spectrometer, which is adapted to introduce a sample to be detected into an inlet of a migration pipe of the ion migration spectrometer, wherein the sampling device comprises: an inner sleeve part, inside of which an inner cavity is defined, wherein one end of the inner sleeve part is connected with the inlet of the migration pipe via an inner-layer channel, and the other end of the inner sleeve part is configured with an inner end cap having an inner opening; and an outer sleeve part, which is configured as an eccentric sleeve that is coaxial with the inner sleeve part and able to rotate with respect to the inner sleeve part, so as to form a sleeve cavity between the inner sleeve part and the outer sleeve part, wherein at least one connecting opening selectively connected with the inner-layer channel is configured at one end of the outer sleeve part, and an outer end cap, on which a first outer opening selectively connected with the inner opening and a second outer opening selectively connected with the sleeve cavity are configured, is configured at the other end of the outer sleeve part, wherein the outer end cap is configured to be able to rotate between a first location and a second location with respect to the inner end cap, so as to selectively introduce a sample to be detected into the inner-layer channel via one of the inner cavity and the sleeve cavity.

In the above embodiment, when the outer end cap is configured to be located in the first location with respect to the inner end cap, the first outer opening on the outer end cap is connected with the inner opening on the inner end cap, the connecting opening is not connected with the inner-layer channel, and the sample to be detected is introduced into the inner-layer channel via the inner cavity; when the outer end cap is configured to be located in the second location with respect to the inner end cap, the first outer opening on the outer end cap is not connected with the inner opening on the inner end cap, the second outer opening on the outer end cap is connected with the sleeve cavity, the connecting opening is connected with the inner-layer channel, and the sample to be detected is introduced into the inner-layer channel via the sleeve cavity.

Preferably, a heating part is configured outside the inner sleeve part, for heating the inner cavity to form a thermal resolving cavity, in which a solid sample to be detected is heated to form a gaseous sample to be detected.

Preferably, a heat insulating layer is further configured outside the heating part, so that heat insulation may be accomplished between the inner sleeve part and the outer sleeve part.

Specifically, the inner opening is configured on one side near the location of the center on the inner end cap; the first outer opening is configured on one side near the location of the center on the outer end cap, and the second outer opening is configured on the other side far from the center and opposite to the first opening on the outer end cap.

More specifically, the inner opening and the first outer opening are rectangular apertures, and the second outer opening comprises a plurality of circular apertures.

In one embodiment, the sampling device for an ion migration spectrometer further comprises: a semipermeable membrane, which is configured between the inlet of the migration pipe and the inner-layer channel, for selectively permeating of a gaseous material to be detected that is introduced into the migration pipe.

Moreover, the sampling device for an ion migration spectrometer further comprises: an enrichment carrier, which is configured between the semipermeable membrane and the inner-layer channel and is adjacent to the location of the semipermeable membrane, for preconcentrating the material to be detected that enters the inner-layer channel.

Specifically, the enrichment carrier is consisted of a plurality of enrichment slices laminated on each other, each of the plurality of enrichment slices comprises: a main body, which is consisted of a metallic film with micropores on the surface thereof or a mesh screen; and an adsorbent, which is attached to the surface of the main body to absorb the material to be detected.

More specifically, the micropores in the plurality of enrichment slices laminated on each other are arranged to interleave with each other, so that when a gas passes through the enrichment carrier vertically, the contact area between the sample gas flow and the adsorbent in the enrichment slices may be increased.

More specifically, the device further comprises: a pulse heating device, which is connected with the enrichment carrier, for performing controllable pulse heating on the enrichment carrier.

According to another aspect of the present invention, it provides a method for introducing a solid sample to be detected by using the above sampling device for an ion migration spectrometer, comprising the steps of: starting the heating part configured outside the inner sleeve part, for continuously heating the inner cavity during the operation process to form a thermal resolving cavity; rotating the outer end cap so as to configure the outer end cap to be located in the first location with respect to the inner end cap; introducing the solid sample to be detected into thermal resolving cavity via the first outer opening on the outer end cap and the inner opening on the inner end cap, wherein in the thermal resolving cavity, the solid sample to be detected is heated to form a gaseous sample to be detected; and introducing the gaseous sample to be detected into the inlet of the migration pipe via the inner-layer channel.

According to a further aspect of the present invention, it provides a method for introducing a gas sample to be detected by using the above sampling device for an ion migration spectrometer, comprising the steps of: starting the heating part configured outside the inner sleeve part, for continuously heating the inner cavity during the operation process to form a thermal resolving cavity; rotating the outer end cap so as to configure the outer end cap to be located in the second location with respect to the inner end cap; introducing a gas sample to be detected into the inner-layer channel via the second outer opening on the outer end cap and the sleeve cavity, and performing preconcentration on the enrichment carrier; rotating the outer end cap after preconcentrating the gas sample to be detected on the enrichment carrier for predetermined time, so as to configure the outer end cap to be located in the first location with respect to the inner end cap; introducing the gas flow to the enrichment carrier via the thermal resolving cavity and activating the pulse heating device connected to the enrichment carrier at the same time, so that the sample to be detected that is preconcentrated on the enrichment carrier is resolved, thereby forming a gaseous sample to be detected; and introducing the gaseous sample to be detected into the inlet of the migration pipe.

According to a further aspect of the present invention, it provides an ion migration spectrometer comprising: a migration pipe, for performing a ionization and migration operation on a sample to be detected that is introduced therein; a gas path device, for supplying carrier gas to the ionization zone and supplying migration gas to the migration zone; and a sampling device as described above, for introducing the sample to be detected into the inlet of the migration pipe.

In the above technical solutions, the ion migration spectrometer further comprises: a sampling pump, for supplying negative pressure to introduce the gas sample to be detected into the sampling device.

Specifically, the migration pipe comprises: an ionization zone, in which molecules of the sample to be detected are ionized to form an ion cluster; and a migration zone, in which an oriented migration and separation process is performed on the ion cluster.

The above unspecified embodiments of the present invention at least have the advantages and effects of the following one or more aspects:

1) The switch of two different locations can be performed between the inner and outer sleeves by employing a structure design of inner and outer sleeves, so that two different gas flow paths are provided selectively. With the above solution, a solid particle sample analyzing function and a low-concentration gas analyzing function are integrated in a single instrument, so that the functions of solid sampling and gas sampling can be compromised by the same sampling device.

2) Moreover, in one embodiment of the present invention, no external gas sample collection and concentration device needs to be equipped, and not only the operation procedure can be simplified and the sensitivity and analyzing efficiency on the gas sample can be improved, but also an effective detection on a trace-amount of a solid sample may be realized at the same time. Specifically, in one embodiment of the invention, the enrichment carrier is configured in a location adjacent to the semipermeable membrane in the sampling device, and the sampling end employs a unique sleeve-type structure design with a rotatable end cap, in the case that the solid sampling function of the instrument is not influenced, by means of controlling the channel that the gas enters and making the best of the heat source of the solid sampling device, low temperature absorption and quick warming up desorption of the gas sample by the enrichment carrier can be realized, so that effective preconcentration may be accomplished, and the instrument is made to have both trace-amount solid particle sample analyzing function and extremely low concentration gas sample analyzing function, without the need for additionally equipping a separate gas collection and concentration device, thereby simplifying the configuration and operation procedure of the instrument and greatly improving the analyzing efficiency of the instrument on gas sample.

3) Moreover, in the present invention, the enrichment carrier is configured in a location adjacent to the semipermeable membrane in the sampling device, the object to be detected that is released during the desorbing process can reach the membrane surface quickly, and a selective permeation process is thus accomplished, so that sample loss in the gas flow channel due to absorption or condensation and deposition can be avoided, and the sensitivity of the instrument can be further improved.

BRIEF DESCRIPTION OF THE DRAWINGS

FIG. 2 is a schematic diagram showing the structure of a sampling device for an ion migration spectrometer according to one specific embodiment of the present invention, in which FIG. 2A is a schematic diagram showing the introduction of a solid particle sample into the sampling device, and FIG. 2B is a schematic diagram showing the introduction of a gas sample into the sampling device.

DETAILED DESCRIPTION OF THE EMBODIMENTS

Figure 1:
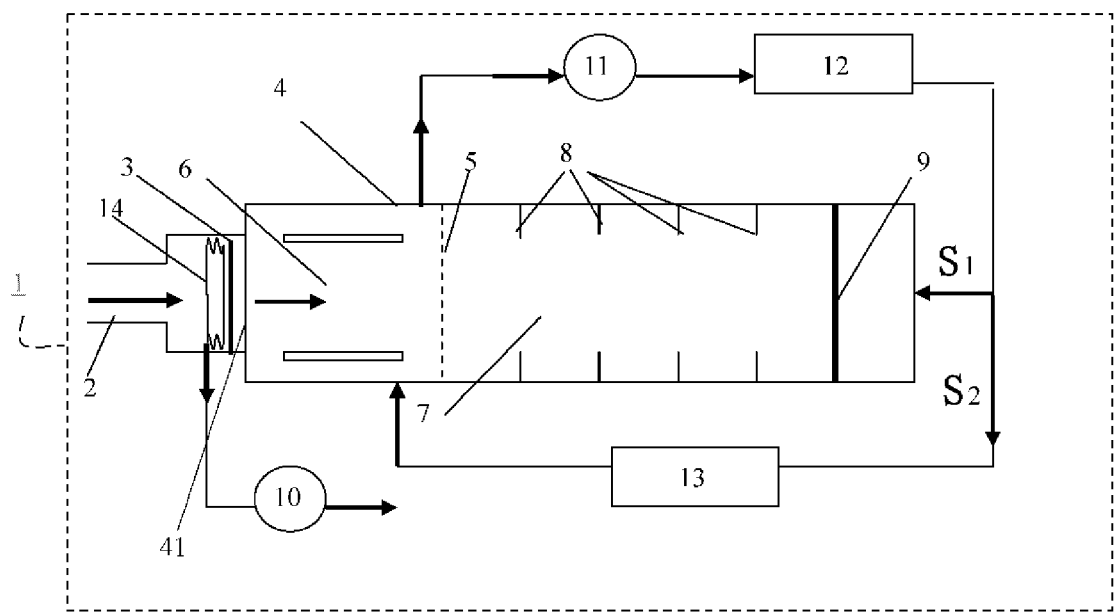
FIG. 1 is a schematic diagram showing the construction and principle of an ion migration spectrometer according to one specific embodiment of the present invention.
Figure 3:
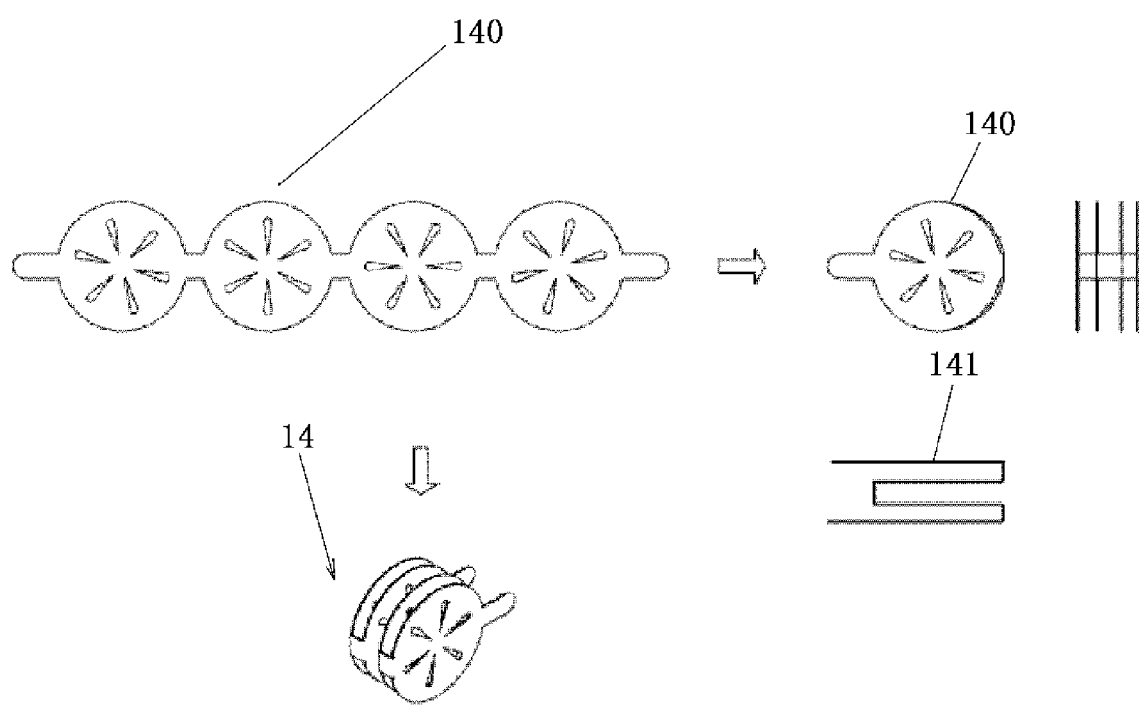
FIG. 3 is a schematic diagram showing an enrichment carrier for an ion migration spectrometer according to one embodiment of the present invention.

The technical solutions of the present invention will now be further illustrated in detail by specific embodiments in conjunction with FIGS. 1-3. In the specification, the same or similar reference number indicates the same or similar part. The following illustrations on the embodiments of the invention referring to the drawings are to explain the general inventive concept of the present invention, and it should not be construed as limiting the scope of the invention.

FIG. 1 is a schematic diagram showing the construction and principle of an ion migration spectrometer according to one specific embodiment of the present invention. As shown in FIG. 1, an ion migration spectrometer 1 according to the present invention comprises: a migration pipe 4, for performing a ionization and migration operation on the sample to be detected that is introduced therein; and a sampling device 2, which has a sampling port for introducing the sample to be detected, wherein the sample to be detected may be introduced into the migration pipe 4 by sucking an air sample containing the gas atmosphere of the object to be detected or by inserting a sampling carrier which has collected the solid particle sample. The sampling device 2 is configured with a permselective semipermeable membrane 3 at the location near an inlet 41 of the migration pipe 4, for isolating the inside of the ion migration spectrometer from the sampling device 2 that is connected with the external environment.

Referring to FIG. 1, the ion migration spectrometer further comprises a sampling pump 10, for supplying negative pressure to introduce the gas sample to be detected into the sampling device 2. Under the action of the sampling pump 10, the molecules of a gaseous material to be detected that is introduced by the sampling device 2 in solid particle or gas sampling mode is brought in front of the semipermeable membrane 3 by an air flow; after being screened by the semipermeable membrane 3, the molecules enter the core element of the ion migration spectrometer 1, that is, an ion migration pipe 4, while the components that cannot permeate the semipermeable membrane 3 are evacuated under the action of the sampling pump 10.

The migration pipe 4 is divided into an ionization reaction zone 6 and a migration zone 7 by an ion gate 5 that can be opened periodically. The molecules of the sample to be detected are ionized in the ionization zone to form ion clusters, and an oriented migration and separation process is accomplished on the resulted ion clusters in the migration zone. In the migration zone 7, a voltage is applied on a cyclic electrode plate 8 to supply an electric field that is uniformly distributed. In the ionization zone 5 of the ion migration pipe 4, the molecules of the object to be detected are ionized and ion clusters are formed, and when the ion gate 5 is opened, the ion clusters enter the migration zone 7 under the action of the electric field and continue to migrate forward under the action of the electric field. In the migration zone 7, the migration speed of the ion clusters are related to such factors as their mass, charge number and volume, etc., thus the times at which different ion clusters arrive at the detector 9 located at the end of the migration zone are different. Therefore, the type of material may be determined by detecting the feeble pulse current from the detector and the arrival time thereof and matching them with the standard material data base.

Moreover, the ion migration spectrometer 1 comprises: a gas path device, for supplying a carrier gas to the ionization zone and supplying a migration gas to the migration zone. The direction of the migration gas flow introduced from the back end of the instrument is opposite to the moving direction of the ions, the migration gas flow is led out from a location near the ion gate 5 in the ionization chamber; and under the propelling of a recycle gas pump 11, a part of the gas that is purified and dried by a filter 12 serves as migration gas flow S1 and enters the rear part of the migration zone, while the other part, that is, gas flow S2, forms a carrier gas flow via a gas path containing a dopant source 13 and enters the ionization reaction zone 6.

The structure and principle of the sampling device for an ion migration spectrometer according to one specific embodiment of the present invention will now be illustrated briefly in conjunction with FIG. 2A-2B.

FIG. 2 shows a sampling device 2 for an ion migration spectrometer, which is adapted to introduce a sample to be detected into an inlet 41 of a migration pipe 4 of an ion migration spectrometer 1, comprising: an inner sleeve part 21, inside of which an inner cavity 23 is defined, wherein one end of the inner sleeve part 21 is connected with the inlet 41 of the migration pipe 4 via an inner-layer channel 24, and the other end of the inner sleeve part 21 is configured with an inner end cap 25 having an inner opening 31; and an outer sleeve part 22, which is configured as an eccentric sleeve that is coaxial with the inner sleeve part 21 and able to rotate with respect to the inner sleeve part 21, so as to form a sleeve cavity 26 between the inner sleeve part 21 and the outer sleeve part 22, wherein one end of the outer sleeve part 22 is configured with at least one connecting opening 27 that is selectively connected with the inner-layer channel 24, and the other end of the outer sleeve part 22 is configured with an outer end cap 28, on which a first outer opening 32 that is selectively connected with the inner opening 31 and a second outer opening 33 that is selectively connected with the sleeve cavity 26 are configured, wherein the outer end cap 28 is configured to be able to rotate between a first location (the location as shown in FIG. 2A) and a second location (the location as shown in FIG. 2B) with respect to the inner end cap 25, so as to selectively introduce a sample to be detected into the inner-layer channel 24 via one of the inner cavity 23 and the sleeve cavity 26. As shown in FIG. 2, the inner-layer channel 24 comprises: a branch channel 24a, which is connected with the inner cavity 23; and a branch channel 24b, which is connected with the sleeve cavity 26 via the connecting opening 27.

Referring to FIG. 2, a heating part 29 is configured outside the inner sleeve part 21, for heating the inner cavity 23 to form a thermal resolving cavity, in which a solid sample to be detected is heated to form a gaseous sample to be detected. One common example is a flat sampling device made of a metallic material such as stainless steel, outside which a heating wire is winded to form a thermal resolving cavity. The sampling device is kept at a high temperature by means of continuously heating, so that the solid sample particles collected on the sampling carrier are heated to be resolved or gasified. The inner-layer channel 24 is configured inside the inner sleeve part 21, wherein under the action of the sampling pump 10, the inner-layer channel 24 introduces an air flow from the sampling device 2 into the inside of the ion migration spectrometer 1.

In the above embodiment, a heat insulating layer 30 is further configured outside the heating part to form a heat insulation between the inner cavity 23 and the sleeve cavity 26. Thus, the sampling device is divided into an inner layer and an outer layer with different temperature, wherein the inner layer is the inner cavity 23 surrounded by the inner sleeve part 21, and it is connected with the branch channel 24a; the outer layer is the sleeve cavity 26 which is consisted of the inner sleeve part 21 and the outer sleeve part 22 that is coaxial with the inner sleeve part 21, and it is selectively connected with the branch channel 24b via the connecting opening 27.

In the above embodiment of the present invention, a mechanism that may control or change the entering of a gas sample into the inner-layer channel 24 is formed. A typical example is as shown in FIG. 2: the inner opening 31 is configured on one side near the location of the center on the inner end cap 25. The outer sleeve part is in the form of an eccentric sleeve that is coaxial with the inner sleeve, and correspondingly, the end cap thereof is in the form of an eccentric circle, of which the outer end cap 28 has several asymmetric openings, wherein the first outer opening 32 is configured in a location adjacent to the center, and it has a shape that is completely coincident with the inner-layer sampling device, each of the rest apertures 33 is distributed at a peripheral location and is connected with the sleeve cavity 26, and a plurality of connecting openings 27 selectively connected with the inner-layer channel 24 are also configured in the sleeve cavity, the locations of the first opening, the second opening and the connecting opening 27 at the end thereof may be changed by rotating the outer sleeve part. Referring to FIG. 2, the first outer opening 32 is configured on one side near the location of the center on the outer end cap 28, and the shape is completely coincident with the inner-layer sampling device; while the second outer opening 33, for example, a plurality of circular apertures, are distributed on the peripheral locations, for example, the second outer opening 33 is configured on the other side far from the center and opposite to the first opening 32 on the outer end cap 28, and it is connected with the sleeve cavity 26. Although in FIG. 2 the inner opening and the first outer opening are rectangular aperture and the second outer opening 33 comprises a plurality of circular apertures, the present invention is not limited hereto, for example, it may employ any suitable shapes.

Referring to FIG. 2, when the outer end cap 28 is configured in the first location with respect to the inner end cap 25 in FIG. 2A to perform solid particles sampling, the first outer opening 32 adjacent to the center of the outer end cap 28 is rotated to a location that is completely coincident with the inner opening 31 on the inner end cap 25, the first outer opening 32 on the outer end cap 28 is connected with the inner opening 31 on the inner end cap 25, the connecting opening 27 is not connected with the eccentric sleeve cavity 26, and the sample to be detected is introduced into the inner-layer channel 24 via the inner cavity 23; when the outer end cap 28 is configured in a second location with respect to the inner end cap 25 in FIG. 2B to perform gas sampling, the outer sleeve part may be rotated so that the first outer opening 32 adjacent to the center is rotated to the side that is opposite to the location on the inner end cap 25, the first outer opening 32 on the outer end cap 28 is not connected with the inner opening 31 on the inner end cap 25, and at this point the eccentric sleeve cavity 26 and the inner-layer channel 24 are connected via a plurality of openings 27, thus the gas may enter the inner-layer channel 24 via the sleeve cavity 26.

The rotation of inner and outer end caps 25 and 28 may be accomplished manually or be automatically realized via a control circuit. An enrichment carrier 14 is configured in a location between the inner-layer channel 24 and the semipermeable membrane 3 and near the semipermeable membrane 3, for preconcentrating the material that is introduced into the migration pipe. Specifically, referring to FIG. 3, the enrichment carrier 14 is consisted of a plurality of enrichment slices 140 laminated on each other, wherein each of the plurality of enrichment slices 140 comprises: a main body 141, which is consisted of a metallic film with micropores on the surface thereof or a mesh screen; and an adsorbent, which is attached to the surface of the main body 141, for absorbing the material to be detected. The mental concerned is generally stainless steel, and an adsorbing material, for example, active carbon powder and so on, is attached to the carrier, or an adsorbent that can absorb the object to be detected is coated on the carrier. Different designs may be employed to make the enrichment carrier have a larger absorbing area, for example, the enrichment carrier may be folded into the shape of waves; moreover, the micropores configured on the surface of each layer of carrier are arranged to interleave with each other, thus when gas passes through the carrier layer vertically, it may flow along the areas between the apertures on the carrier surface, so that the contact area between the sample gas flow and the adsorbent on the carrier collecting surface is increased. In one embodiment, the device further comprises a pulse heating device (not shown) connected with the enrichment carrier 14, by which controllable pulse heating may be conducted on the enrichment carrier 14.

The specific operation of solid particle sampling and gas sampling by using the above sampling device will be illustrated below in conjunction with the drawings.

Before the sampling operation, a heating part 29 configured outside the inner sleeve part is started, for continuously heating the inner cavity 23 during the operation process to form a thermal resolving cavity. When solid particle sampling is performed, as shown in FIG. 2A, the outer end cap 28 is rotated so as to be configured in a first location shown in FIG. 2A with respect to the inner end cap; the solid sample to be detected is introduced into a thermal resolving cavity that is formed via the first outer opening 32 on the outer end cap 28 and the inner opening 31 on the inner end cap 25, and in the thermal resolving cavity, the solid sample to be detected is heated to form a gaseous sample to be detected; and the gaseous sample to be detected is introduced into the inlet 41 of the migration pipe 4 via the inner-layer channel 24.

When gas sampling is performed, as shown in FIG. 2B, the outer end cap 28 is rotated so as to be configured in a second location shown in FIG. 2B with respect to the inner end cap 25; a gas sample to be detected is introduced into the inner-layer channel 24 via the second outer opening 32 on the outer end cap 28 and the sleeve cavity 26, and it is preconcentrated on the enrichment carrier 14; after the gas sample to be detected is preconcentrated on the enrichment carrier 14 for a predetermined time, the outer end cap 28 is rotated so as to be configured in the first location shown in FIG. 2A with respect to the inner end cap 25; the gas flow is introduced onto the enrichment carrier 14 via thermal resolving cavity, and the pulse heating device connected to the enrichment carrier is selectively activated to gasify and resolve the sample to be detected that is preconcentrated on the enrichment carrier 14; and the gaseous sample to be detected is introduced into the inlet 41 of the migration pipe 4 via the inner-layer channel 24.

In a practical detection process, thermal resolving cavity 23 of the sampling device of the ion migration spectrometer 1 is always in a continuously heating state, and when solid sampling is performed, the outer sleeve part 22 of the sampling device 2 is rotated to the first location shown in FIG. 2A, so that the opening 32 on its end, which is adjacent to the center, is connected with the inner opening 31 on the inner end cap 25, while its connecting opening 27 is not connected with the sleeve cavity 26, and the gas enters the inside of the ion migration spectrometer 1 via thermal resolving cavity 23. A solid sampling carrier is inserted into the sampling device 2 via the above inner opening 31 and outer opening 32, and the solid particle sample collected by the carrier is gasified and enters the ion migration spectrometer 1 along with the air flow for analyzing.

When gas sampling is performed by the ion migration spectrometer 1, the outer sleeve part 22 is first rotated to the second location shown in FIG. 2B, so that the opening 32 on its outer end cap 28, which is near the center, is rotated to the side opposite to the inner opening 31 on the inner end cap 25, while its connecting opening 27 is connected with the sleeve cavity 26, and the gas enters the inner-layer channel 24 via the sleeve cavity 26. Because a heat insulating layer exists between the sleeve cavity 26 and thermal resolving cavity 23, the temperature of the gas introduced into the inner-layer channel 24 via the sleeve cavity 26 is close to the ambient temperature, and the temperature is still low when it passes through the enrichment carrier 14, which is favourable for the effective absorbing of the gas sample; after the gas sample is collected for a certain period of time, the outer sleeve part 22 is rotated to the first location shown in FIG. 2A, that is, the location corresponding to the location of solid particles sampling ; at this point, the gas enters the ion migration spectrometer 1 from thermal resolving cavity 23 under the action of the sampling pump 10.

At this moment, because the gas flow passes through thermal resolving cavity 23 that is at a high temperature, the temperature of the gas flow will be increased quickly. When the gas flow passes through the enrichment carrier 14, the enrichment carrier 14 made of metallic material will be heated, and at the same time, the pulse heating function of the enrichment carrier 14 may also be activated, so that the temperature of the carrier will be increased rapidly, thereby releasing the material to be detected that is absorbed. Because the air resistance in the gas flow path is low during gas collection, flow rate of gas is large in the sample collection or absorption process, thus more gas atmosphere of the object to be detected may be sucked in; however, because the gas path is narrow and the flow rate of gas is small during the desorbing process, the component absorbed is released into the gas flow which has a small flow rate, so that the concentration effect may be enhanced. Moreover, because the enrichment carrier 14 is configured in a location that is near the semipermeable membrane 3, the object to be detected that is released during the desorbing process can quickly reach the surface of the semipermeable membrane 3, and a selective permeation process is thus accomplished. Thereby, sample loss in the gas flow channel due to absorption or condensation and deposition can be avoided, and the sensitivity of the ion migration spectrometer 1 can be further improved.

Although some embodiments of the general inventive concept have been shown and illustrated, it will be understood by one skilled in the art that various modifications can be made to these embodiments without departing from the spirit or scope of the general inventive concept, and the scope of the invention will be defined by the claims and their equivalents.

What is claimed is:

1. A sampling device for an ion migration spectrometer, which is adapted to introduce a sample to be detected into an inlet of a migration pipe of the ion migration spectrometer, wherein the sampling device comprises:
    an inner sleeve part, inside of which an inner cavity is defined, one end of the inner sleeve part is connected with the inlet of the migration pipe via an inner-layer channel, and the other end of the inner sleeve part is configured with an inner end cap having an inner opening; and
    an outer sleeve part, which is configured as an eccentric sleeve that is coaxial with the inner sleeve part and able to rotate with respect to the inner sleeve part, so as to form a sleeve cavity between the inner sleeve part and the outer sleeve part, one end of the outer sleeve part is configured with at least one connecting opening that is selectively connected with the inner-layer channel, and the other end of the outer sleeve part is configured with an outer end cap, on which a first outer opening selectively connected with the inner opening and a second outer opening selectively connected with the sleeve cavity are configured,
    wherein, the outer end cap is configured to be able to rotate between a first location and a second location with respect to the inner end cap, so as to selectively introduce a sample to be detected into the inner-layer channel via one of the inner cavity and the sleeve cavity.

2. The sampling device for an ion migration spectrometer according to claim 1, wherein:
    when the outer end cap is configured to be located in the first location with respect to the inner end cap, the first outer opening on the outer end cap is connected with the inner opening on the inner end cap, the connecting opening is not connected with the inner-layer channel, and the sample to be detected is introduced into the inner-layer channel via the inner cavity;
    when the outer end cap is configured to be located in the second location with respect to the inner end cap, the first outer opening on the outer end cap is not connected with the inner opening on the inner end cap, the second outer opening on the outer end cap is connected with the sleeve cavity, the connecting opening is connected with the inner-layer channel, and the sample to be detected is introduced into the inner-layer channel via the sleeve cavity.

3. The sampling device for an ion migration spectrometer according to claim 1, wherein:
    a heating part is configured outside the inner sleeve part, for heating the inner cavity to form a thermal resolving cavity, in which a solid sample to be detected is heated to form a gaseous sample to be detected.

4. The sampling device for an ion migration spectrometer according to claim 3, wherein:
    a heat insulating layer is further configured outside the heating part, for forming heat insulation between the inner sleeve part and the outer sleeve part.

5. The sampling device for an ion migration spectrometer according to claim 3, wherein:
    the inner opening is configured on one side near the location of the center on the inner end cap; and
    the first outer opening is configured on one side near the location of the center on the outer end cap, and the second outer opening is configured on the other side far from the center and opposite to the first opening on the outer end cap.

6. The sampling device for an ion migration spectrometer according to claim 5, wherein:
    the inner opening and the first outer opening are rectangular apertures, and the second outer opening comprises a plurality of circular apertures.

7. The sampling device for an ion migration spectrometer according to claim 4, further comprising:
    a semipermeable membrane, which is configured between the inlet of the migration pipe and the inner-layer channel, for filtering a gaseous material introduced into the migration pipe.

8. The sampling device for an ion migration spectrometer according to claim 7, further comprising:
    an enrichment carrier, which is configured between the semipermeable membrane and the inner-layer channel and is adjacent to the location of the semipermeable membrane, for preconcentrating the material to be detected that enters the inner-layer channel.

9. The sampling device for an ion migration spectrometer according to claim 8, wherein:
    the enrichment carrier consists of a plurality of enrichment slices laminated on each other, each of the plurality of enrichment slices comprises:

a main body, which consists of a metallic film with micropores on the surface thereof; and an adsorbent, which is attached to the surface of the main body, for absorbing the material to be detected.

10. The sampling device for an ion migration spectrometer according to claim 9, further comprising:

a pulse heating device, which is connected to the enrichment carrier, for performing controllable pulse heating on the enrichment carrier.

11. The sampling device for an ion migration spectrometer according to claim 9, wherein:

the micropores in the plurality of enrichment slices laminated on each other are arranged to interleave with each other, so that when a gas passes through the enrichment carrier vertically, the contact area between the sample gas flow and the adsorbent in the enrichment slices is increased.

12. A method for introducing a solid sample to be detected by using the sampling device for an ion migration spectrometer according to claim 3, comprising the steps of:

starting the heating part configured outside the inner sleeve part, for continuously heating the inner cavity during the operation process to form a thermal resolving cavity;

rotating the outer end cap, so as to configure the outer end cap to be located in the first location with respect to the inner end cap;

introducing the solid sample to be detected into the thermal resolving cavity via the first outer opening on the outer end cap and the inner opening on the inner end cap, wherein in the thermal resolving cavity, the solid sample to be detected is heated to form a gaseous sample to be detected; and introducing the gaseous sample to be detected into the inlet of the migration pipe via the inner-layer channel.

13. A method for introducing a gas sample to be detected by using the sampling device for an ion migration spectrometer according to claim 8, comprising the steps of:

starting the heating part configured outside the inner sleeve part, for continuously heating the inner cavity during an operation process to form a thermal resolving cavity;

rotating the outer end cap, so as to configure the outer end cap to be located in the second location with respect to the inner end cap;

introducing the gas sample to be detected into the inner-layer channel via the second outer opening on the outer end cap and the sleeve cavity, and performing preconcentration on the enrichment carrier;

rotating the outer end cap after preconcentrating the gas sample to be detected on the enrichment carrier for a predetermined time, so as to configure the outer end cap to be located in the first location with respect to the inner end cap;

introducing the gas flow to the enrichment carrier via the thermal resolving cavity, so as to resolve the sample to be detected that is preconcentrated on the enrichment carrier and form a gaseous sample to be detected; and introducing the gaseous sample to be detected into the inlet of the migration pipe via the inner-layer channel.

14. The method for introducing a gas sample to be detected by using the sampling device for an ion migration spectrometer according to claim 13, further comprising the steps of:

starting the pulse heating device connected to the enrichment carrier, for performing controllable pulse heating on the enrichment carrier.

15. An ion migration spectrometer, comprising:

a migration pipe, for performing an ionization and migration operation on the sample to be detected that is introduced therein;

a gas path device, for supplying a carrier gas to an ionization zone and supplying a migration gas to a migration zone; and the sampling device according to claim 1, for introducing the sample to be detected into the inlet of the migration pipe.

16. The ion migration spectrometer according to claim 15, further comprising:

a sampling pump, for supplying negative pressure to introduce the gas sample to be detected into the sampling device.

17. The ion migration spectrometer according to claim 15, wherein, the migration pipe comprises:

the ionization zone, in which molecules of the sample to be detected are ionized to form an ion cluster; and the migration zone, in which an oriented migration and separation process is performed on the ion cluster.

\* \* \* \* \*

UNITED STATES PATENT AND TRADEMARK OFFICE
CERTIFICATE OF CORRECTION

PATENT NO. : 8,304,716 B2  
APPLICATION NO. : 13/170763  
DATED : November 6, 2012  
INVENTOR(S) : Zhiqiang Chen et al.

Page 1 of 1

It is certified that error appears in the above-identified patent and that said Letters Patent is hereby corrected as shown below:

Title page, item (30) add Foreign Application Priority Data

Dec. 31, 2010    (CN) ...................... 201010624253.8

Signed and Sealed this
Second Day of April, 2013

Teresa Stanek Rea
*Acting Director of the United States Patent and Trademark Office*